US006663627B2

(12) United States Patent
Francischelli et al.

(10) Patent No.: US 6,663,627 B2
(45) Date of Patent: Dec. 16, 2003

(54) ABLATION SYSTEM AND METHOD OF USE (75) Inventors: David E. Francischelli, Anoka, MN (US); Eduardo N. Warman, Maple Grove, MN (US); Rahul Mehra, Stillwater, MN (US); Mark T. Stewart, Lino Lakes, MN (US); James R. Skarda, Lake Elmo, MN (US); Harry Puryear, Shoreview, MN (US); David Schwartzman, Pittsburgh, PA (US)

(73) Assignee: Medtronic, Inc., Minneapolis, MN (US)

( * ) Notice: Subject to any disclaimer, the term of this patent is extended or adjusted under 35 U.S.C. 154(b) by 31 days.

(21) Appl. No.: 10/132,392

(22) Filed: Apr. 24, 2002

(65) Prior Publication Data
US 2002/0183736 A1 Dec. 5, 2002

Related U.S. Application Data
(60) Provisional application No. 60/286,923, filed on Apr. 26, 2001.

(51) Int. Cl.$^7$ ............................................. A61B 18/18
(52) U.S. Cl. ........................ 606/41; 606/34; 607/122
(58) Field of Search ....................... 606/32–34, 41, 606/42; 607/101, 102, 116, 122; 600/508, 510

(56) References Cited

U.S. PATENT DOCUMENTS

| 5,215,103 A | * | 6/1993 | Desai ............................ 606/46 |
| 5,233,515 A | | 8/1993 | Cosman |
| 5,246,438 A | * | 9/1993 | Langberg |
| 5,450,846 A | * | 9/1995 | Goldreyer |
| 5,540,681 A | | 7/1996 | Strul et al. ..................... 606/34 |
| 5,540,684 A | | 7/1996 | Hassler, Jr. .................... 606/40 |
| 5,558,671 A | | 9/1996 | Yates .......................... 606/38 |
| 5,562,721 A | | 10/1996 | Marchlinski et al. ......... 607/99 |
| 5,579,764 A | * | 12/1996 | Goldreyer |
| 5,690,611 A | | 11/1997 | Swartz et al. ................ 604/53 |
| 5,733,280 A | | 3/1998 | Avitall ........................ 606/23 |
| 5,897,533 A | | 4/1999 | Glickman ................... 604/256 |
| 5,916,213 A | | 6/1999 | Haissaguerre et al. ........ 606/41 |
| 5,957,961 A | | 9/1999 | Maguire et al. .............. 607/99 |
| 6,066,136 A | * | 5/2000 | Geistert |
| 6,183,468 B1 | * | 2/2001 | Swanson et al. .............. 606/40 |
| 6,322,558 B1 | * | 11/2001 | Taylor et al. ................. 606/34 |
| 6,423,057 B1 | * | 7/2002 | He et al. ...................... 606/34 |
| 2003/0004507 A1 | * | 1/2003 | Francischelli et al. ........ 606/41 |

* cited by examiner

Primary Examiner—Michael Peffley
(74) Attorney, Agent, or Firm—Thomas G. Berry; Daniel W. Latham (57) ABSTRACT A system and method for creating lesions and assessing their completeness or transmurality. Assessment of transmurality of a lesion is accomplished by monitoring the depolarization signal amplitude in a local electrogram taken using electrodes located adjacent the tissue to be ablated. Following onset of application of ablation energy to heart tissue, the amplitude of a local electrogram measured with electrodes located adjacent tissue to be ablated first gradually drops and then stabilizes, indicating that the tissue being monitored has ceased making any contribution to the sensed electrogram. The amplitude drop and/or the following amplitude plateau may be used alone or together as indicators of transmurality. Detection of a rapid drop in amplitude may be employed as an indicator that the ablation process is proceeding too quickly and may be employed to trigger a reduction in the power of applied ablation energy. Detection of an insufficiently rapid drop in amplitude may be employed as an indicator that the ablation process is proceeding too slowly and may be employed to trigger an increase in the power of applied ablation energy.

20 Claims, 11 Drawing Sheets

ABLATION SYSTEM AND METHOD OF USE

RELATED U.S. APPLICATION DATA

This application claims priority to Provisional U.S. Patent Application No. 60/286,923, filed Apr. 26, 2001 by Franschelli et al., incorporated herein by reference in its entirety.

BACKGROUND OF THE INVENTION

The present invention relates to tissue ablation devices generally and relates more particularly to devices adapted to ablate lines of tissue, for example for use in conjunction with an electrosurgical version of the Maze procedure.

The Maze procedure is a surgical intervention for patients with chronic atrial fibrillation (AF) that is resistant to other medical treatments. The operation employs incisions in the right and left atria which divide the atria into electrically isolated portions which in turn results in an orderly passage of the depolarization wave front from the sino-atrial node (SA Node) to the atrial-ventricular node (AV Node) while preventing reentrant wave front propagation. Although successful in treating AF, the surgical Maze procedure is quite complex and is currently performed by a limited number of highly skilled cardiac surgeons in conjunction with other open-heart procedures. As a result of the complexities of the surgical procedure, there has been an increased level of interest in procedures employing electrosurgical devices or other types of ablation devices, e.g. thermal ablation, microwave ablation, cryo-ablation or the like to ablate tissue along pathways approximating the incisions of the Maze procedure. Electrosurgical systems for performing such procedures are described in U.S. Pat. No. 5,916,213, issued to Hiassaguerre, et al. U.S. Pat. No. 5,957,961, issued to Maguire, et al. and U.S. Pat. No. 5,690,661, all incorporated herein by reference in their entireties. Cryo-ablation systems for performing such procedures are described in U.S. Pat. No. 5,733,280 issued to Avitall, also incorporated herein by reference in its entirety.

In conjunction with the use of electrosurgical ablation devices, various control mechanisms have been developed to control delivery of ablation energy to achieve the desired result of ablation, i.e. killing of cells at the ablation site while leaving the basic structure of the organ to be ablated intact. Such control systems include measurement of temperature and impedance at or adjacent to the ablation site, as are disclosed in U.S. Pat. No. 5,540,681, issued to Struhl, et al., incorporated herein by reference in its entirety.

Additionally, there has been substantial work done toward assuring that the ablation procedure is complete, i.e. that the ablation extends through the thickness of the tissue to be ablated, before terminating application of ablation energy. This desired result is some times referred to as a "transmural" ablation. For example, detection of a desired drop in electrical impedance at the electrode site as an indicator of transmurality is disclosed in U.S. Pat. No. 5,562,721 issued to Marchlinski et al, incorporated herein by reference in its entirety. Alternatively, detection of an impedance rise or an impedance rise following an impedance fall are disclosed in U.S. Pat. No. 5,558,671 issued to Yates and U.S. Pat. No. 5,540,684 issued to Hassler, respectively, also incorporated herein by reference in their entireties. Because ablated heart tissue is necrotic, it does not depolarize and therefore does not contribute to the depolarization signal. This fact has recently led some physicians to use the amplitude of a locally acquired electrogram signal to determine whether a lesion is complete. For example, during provision of R-F energy at a constant power level, the physician may monitor the amplitude of electrograms obtained using electrodes adjacent the ablation site, and, in response to a defined drop, e.g. 75%, may terminate provision of RF energy.

Three basic approaches have been employed to create elongated lesions using electrosurgical devices. The first approach is simply to create a series of short lesions using a contact electrode, moving it along the surface of the organ wall to be ablated to create a linear lesion. This can be accomplished either by making a series of lesions, moving the electrode between lesions or by dragging the electrode along the surface of the organ to be ablated and continuously applying ablation energy, as described in U.S. Pat. No. 5,897,533 issued to Mulier, et al., incorporated herein by reference in its entirety. The second basic approach to creation of elongated lesions is simply to employ an elongated electrode, and to place the elongated electrode along the desired line of lesion along the tissue. This approach is described in U.S. Pat. No. 5,916,213, cited above and. The third basic approach to creation of elongated lesions is to provide a series of electrodes and arrange the series of electrodes along the desired line of lesion. The electrodes may be activated individually or in sequence, as disclosed in U.S. Pat. No. 5,957,961, also cited above. In the case of multi-electrode devices, individual feedback regulation of ablated energy applied via the electrodes may also be employed. The present invention is believed useful in conjunction with all three approaches

SUMMARY OF THE INVENTION

The present invention is directed toward an improved system for creating lesions and assessing their completeness or transmurality. In the preferred embodiment as disclosed, the apparatus for producing the lesions is an electrosurgical device, in particular a saline-irrigated bipolar electrosurgical forceps. However, the mechanism for assessing lesion transmurality provided by the present invention is believed useful in other contexts, including unipolar R-F ablation and R-F ablation using catheters or hand-held probes. The mechanism for assessing transmurality may also be of value in the context of other types of ablation systems, including those in which ablation occurs in conjunction with an induced rise in tissue temperature, such as those applying ablation energy in the form of microwave radiation, light (laser ablation) or heat (thermal ablation). The invention may also be useful in conjunction with other types of ablation, including cryo-ablation, ultrasound ablation and chemical ablation.

According to the present invention, assessment of transmurality of a lesion is accomplished by monitoring the depolarization signal amplitude in a local electrogram taken using electrodes located adjacent the tissue to be ablated. In the context of R-F ablation, measurement of electrogram amplitude may be done using the ablation electrodes or may be done using dedicated electrodes adjacent to the ablation electrodes. In the context of the other types of ablation discussed above, electrogram measurement would typically be accomplished by means of a dedicated set of measurement electrodes.

Following onset of application of ablation energy to heart tissue, the amplitude of a local electrogram measured with electrodes located adjacent tissue to be ablated first gradually drops and then stabilizes, indicating that the tissue being monitored has ceased making any contribution to the sensed electrogram. The amplitude drop ($\Delta$EGM) or the following amplitude plateau "P" may be used alone or together as indicators of transmurality employed by the present invention. The amplitude drop may be compared to a pre-set value ($\Delta$EGM ? a). (The plateau "P" may be detected in response to a determination that the rate of amplitude change is less than a defined value over a series of amplitude measurements or over a defined duration ($|dA/dt|$=b). In some embodiments, detection of a rapid drop in amplitude (dA/dt=d) may be employed as an indicator that the ablation process is proceeding too quickly and may be employed to trigger a reduction in the power of applied ablation energy. In other embodiments, detection of an insufficiently rapid drop in amplitude (dA/dt=d) may be employed as an indicator that the ablation process is proceeding too slowly and may be employed to trigger an increase in the power of applied ablation energy.

In the context of R-F ablation, the invention is believed valuable in conjunction with an ablation device having multiple, individually activatable electrodes or electrode pairs to be arranged along a desired line of lesion. In this context, the mechanism for determining transmurality of lesions adjacent individual electrodes or pairs may be used to deactivate individual electrodes or electrode pairs, when the lesions in tissue adjacent these individual electrodes or electrode pairs are complete. This allows the creation of an essentially uniform lesion along the line of electrodes or electrode pairs, regardless of differences in tissue thickness adjacent the individual electrodes or electrode pairs. The invention is also believed useful in conjunction with assessment of transmurality of lesions produced by devices having only a single electrode or single electrode pair. Similar considerations apply to the use of the present invention in the contexts of other types of ablation as listed above.

DETAILED DESCRIPTION OF PREFERRED EMBODIMENTS

Figure 1:
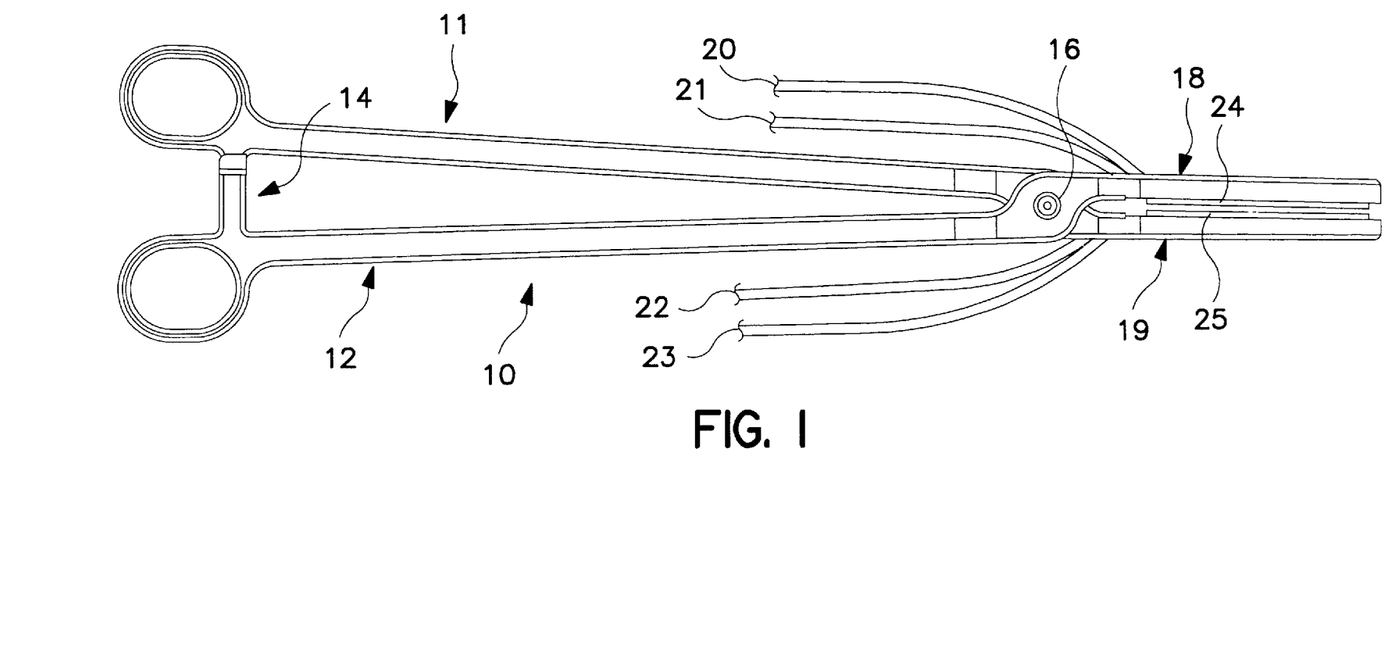
FIG. 1 is a plan view of a type of electrosurgical hemostat that may be used in conjunction with the present invention.

FIG. 1 is a plan view of a bipolar, saline irrigated electrosurgical hemostat of a type that may be employed in conjunction with the present invention. The hemostat is provided with elongated handles 11 and 12 and a lock mechanism 14, similar to a conventional surgical hemostat. The handles are connected to one another by pivot or hinge 16, and continue distally in the form of elongated jaws 18 and 19. Jaws 18 and 19 carry an elongated electrode or series of electrodes 24, 25, respectively, to which ablation energy, e.g. RF energy is applied by means of conductors 21 and 22. The electrodes are adapted to be irrigated by a saline solution or other conductive fluid along their length, provided via inlet tubes 20 and 23. In operation, tissue to be ablated is compressed between the jaws, and RF energy is applied between the electrode or electrode sets 24 and 25, as generally described in U.S. Pat. No. 6,096,037 issued to Mulier et al incorporated herein by reference in its entirety.

Figure 2A:
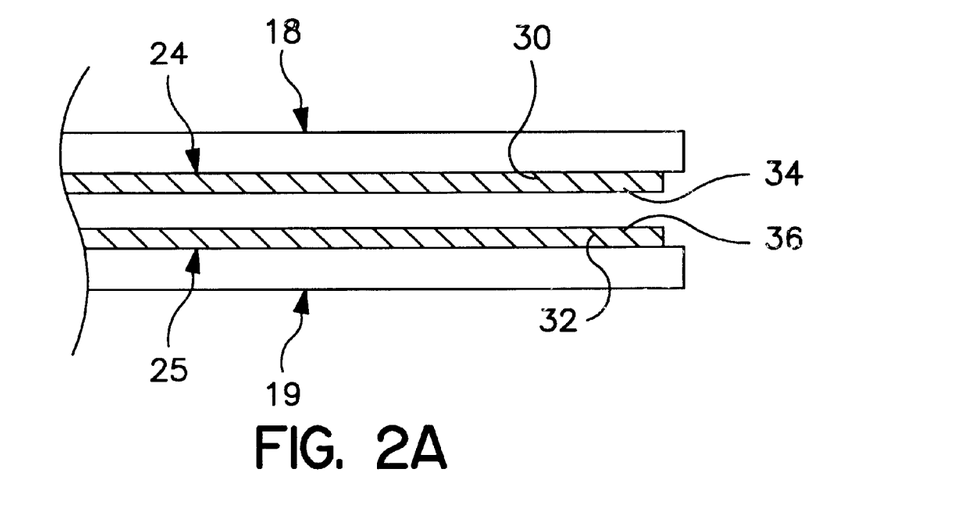
FIGS. 2a and 2b illustrate alternative electrode configurations for a hemostat generally according to FIG. 1.

FIG. 2a shows a first embodiment of an electrode arrangement for a hemostat generally as illustrated in FIG. 1. Illustrated components correspond to identically numbered components in FIG. 1. In this embodiment, electrodes 24 and 25 take the form of elongated coil electrodes 30 and 32, mounted around porous tubes 34 and 36, through which saline or other conductive fluid is delivered. The arrangement of the electrodes may also be reversed, for example placing coils 30 and 32 within elongated porous tubes 34 and 36, to accomplish a similar result. Alternatively, any other arrangement for providing an elongated electrode and delivery of saline solution along the length thereof may be substituted. The particular configuration of the electrode is not critical to the present invention. For example, irrigated electrodes corresponding to those described in U.S. Pat. No. 6,096,037 issued to Mulier, et al., U.S. Pat. No. 5,876,398 issued to Mulier, et al., U.S. Pat. No. 6,017,378 issued to Brucker, et al or U.S. Pat. No. 5,913,856 issued to Chia, et al., all incorporated herein by reference in their entireties may also be substituted. It should also be noted that while the electrode system as illustrated in FIG. 2a is a bipolar system, the invention may also be employed in conjunction with unipolar electrodes and/or in the form of a probe or a catheter. In some embodiments, irrigation of the electrodes may be omitted.

Figure 2B:
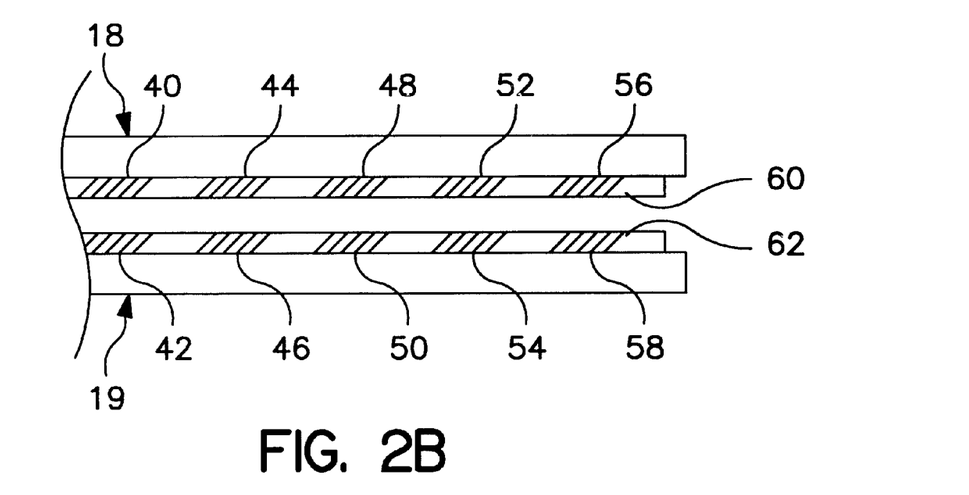

FIG. 2b illustrates an alternative embodiment of an electrode system for a hemostat generally as illustrated in FIG. 1. In this case, rather than a single pair of electrodes, multiple electrode pairs are provided. The electrode pairs comprise coil electrodes 40 and 42, 44 and 46, 48 and 50, 52 and 54, and 56 and 58. However, other pairings of electrodes might also be substituted, for example, pairing electrodes 40 and 44, electrodes 48 and 52 or the like. In this embodiment, the electrode pairs are mounted around porous plastic tubes 60 and 62 through which saline or other electrically conductive fluid is delivered. As in the case with the embodiment of FIG. 2a, the arrangement of these electrodes may readily be reversed, placing the electrodes within the lumen of plastic tube 60 or 62 and any other arrangement providing multiple, irrigated electrodes may also be substituted. As in the case of the embodiment of FIG. 2a, unipolar electrodes might be substituted for the multiple bipolar pairs as illustrated and/or the invention may be practiced in conjunction with a multi-electrode probe or catheter.

In use, the hemostat is arranged so that the tissue to be ablated is located between the jaws 18 and 19, and pressure is applied in order to compress the tissue slightly between the jaws to ensure good electrical contact. All electrode pairs may be activated individually and may be individually deactivated when the lesions between the individual electrode pairs are completely transmural. Alternatively, electrode pairs could be activated sequentially, with one pair deactivated upon a detection of a complete lesion between the electrode pair, followed by activation of the next sequential electrode pair. Corresponding use of the invention in conjunction with a series of unipolar electrodes, for example corresponding to electrodes along one of the two jaws in conjunction with a remote ground plate or a similar series of individually activatable electrodes on a catheter or probe in conjunction with a ground plate is also possible.

Figure 3:
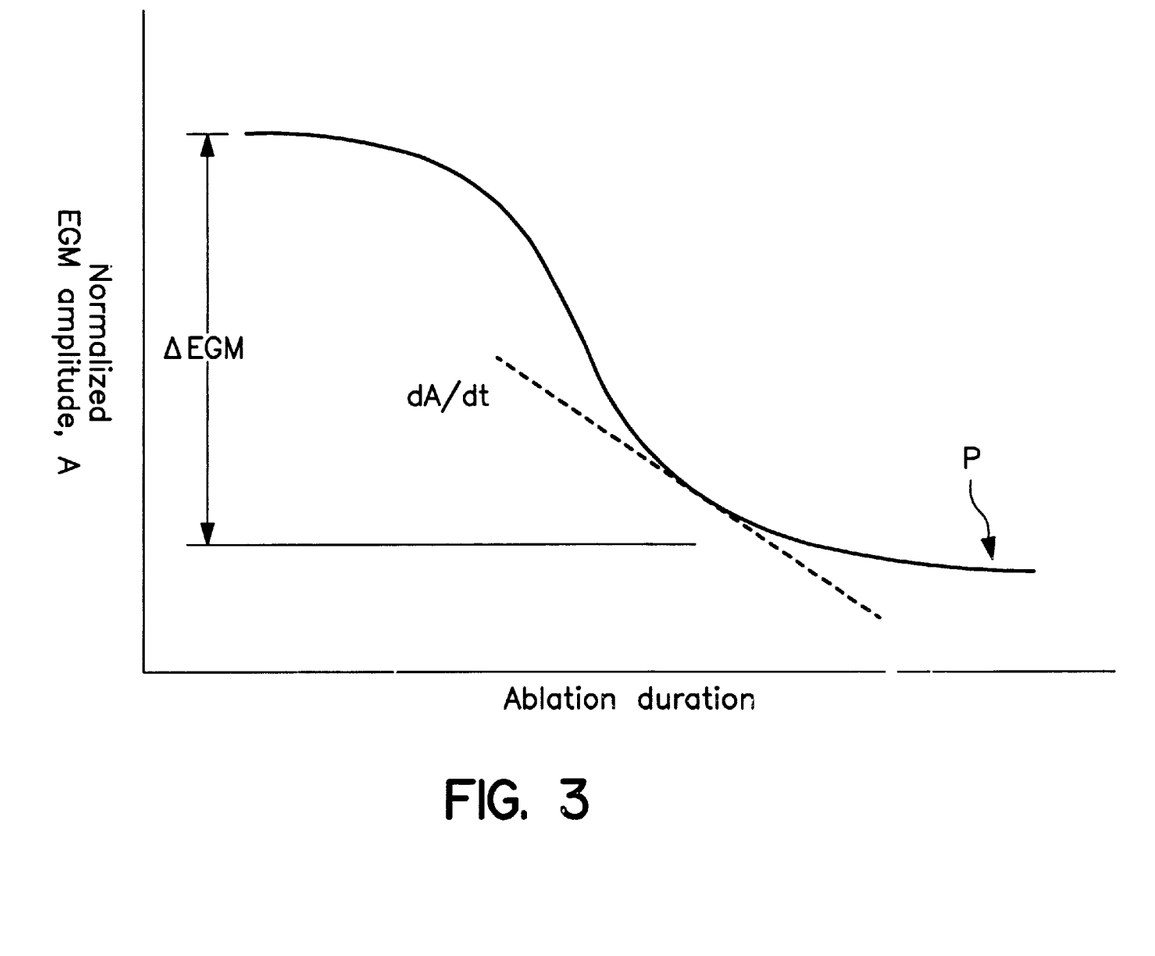
FIG. 3 illustrates the fall and plateau of electrogram amplitude measured using electrodes adjacent tissue during ablation.

FIG. 3 is a graph illustrating measured local electrogram amplitude "A" vs. time across tissue located between the electrodes of an irrigated bipolar hemostat as illustrated in FIG. 1. FIG. 3 illustrates the drop in electrogram amplitude followed by an amplitude plateau. The amplitude drop (ΔEGM) or the following amplitude plateau "P" may be used alone or together as indicators of transmurality employed by the present invention. In some embodiments, detection of a rapid rate of drop in amplitude (dA/dT) may be employed as an indicator that the ablation process is proceeding too quickly and may be employed to trigger a reduction in the power of applied ablation energy. In other embodiments, detection of an insufficient rate of drop in amplitude (dA/dT) may be employed as an indicator that the ablation process is proceeding too slowly and may be employed to trigger an increase in the power of applied ablation energy.

Figure 4:
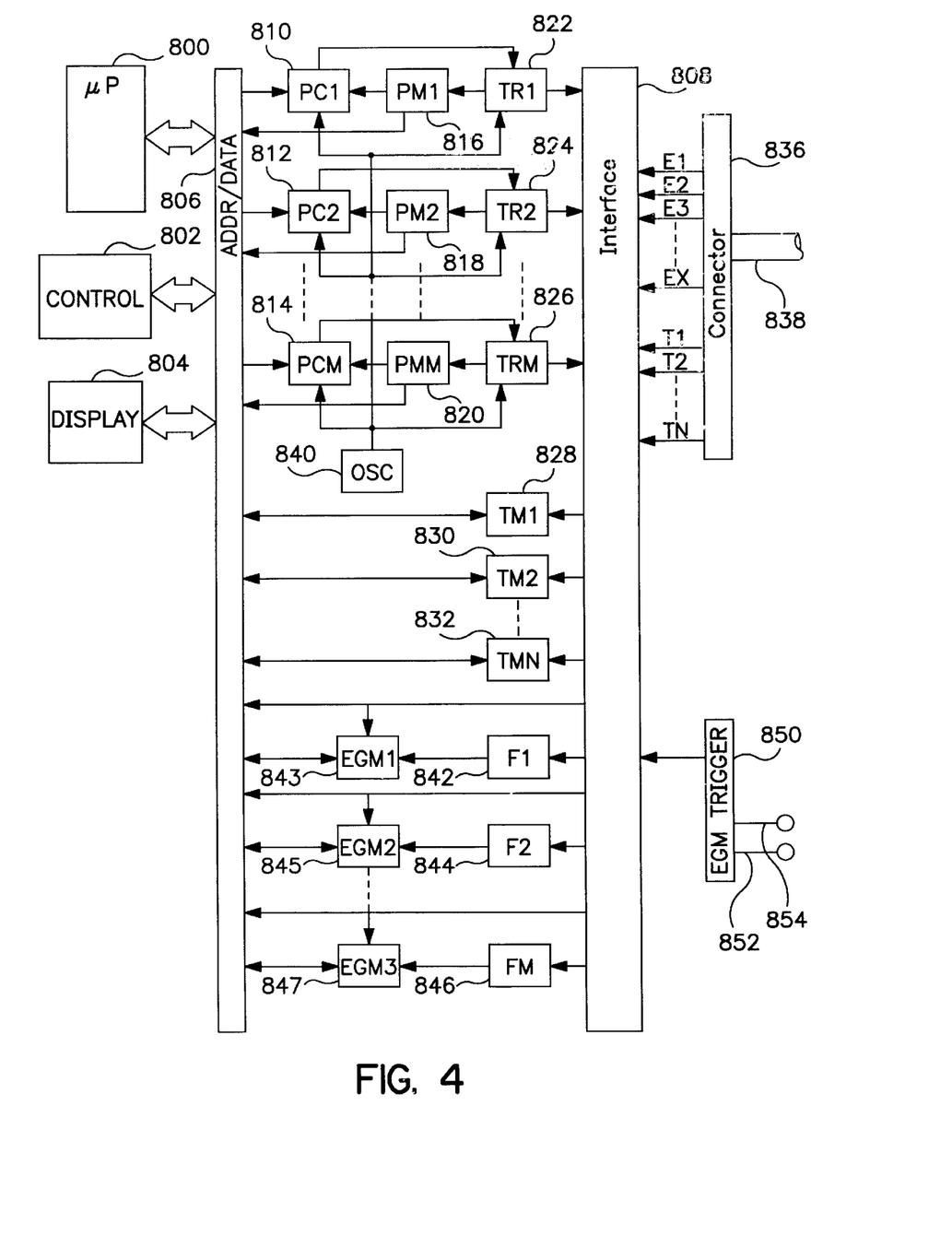
FIG. 4 is a functional block diagram of an RF generator appropriate for use in practicing the present invention, particularly adapted for use in conjunction with an ablation system employing multiple, individually activatable electrodes or electrode pairs.

FIG. 4 is a functional block diagram illustrating one embodiment of an R-F generator system for use in conjunction with the present invention. In this embodiment, separately controllable R-F outputs are provided for individual ablation electrodes or electrode pairs on an associated R-F ablation device, for example as in FIG. 2B. The R-F generator could of course also be used with ablation devices having only a single electrode or electrode pair as in FIG. 2A. With the exception of the electrogram amplitude measurement circuits discussed below, the generator corresponds generally to that described in conjunction with FIG. 16 of the '961 patent issued to Maguire, et al., cited above. The RF generator disclosed in the '961 patent provides feedback control of R-F power based upon either measured power (constant power) or measured temperature. The present invention is somewhat easier to implement in conjunction with the constant power mode, but may also be adapted to a temperature-regulated mode or to other feedback power regulation mechanism.

Display 804 and controls 802 are connected to a digital microprocessor 800, which permits interface between the user and the remainder of the electrical components of the system. Microprocessor 800 operates under control of stored programming defining its operation including programming controlling its operation according to the present invention, as discussed in more detail below. Microprocessor 800 provides control outputs to and receives input signals from the remaining circuitry via address/data bus 806. In particular, the microprocessor 800 provides for monitoring of power, current, voltage, electrogram amplitude and temperature. As necessary, the microprocessor will provide this information to the display 804. Additionally, the microprocessor 800 permits the user to select the control mode (either temperature or power) and to input the power set point,
temperature set point, and a timer set point to the system. The primary source of power for the radio-frequency generator may be a 12 V battery rated at 7.2 ampere-hours or the device may be AC powered. A back-up battery (not shown) such as a lithium cell may also be provided to provide sufficient power to the microprocessor 260 to maintain desired memory functions when the main power is shut off.

The power supply system as illustrated includes a desired number "M" of individually controllable R-F power supplies and receives temperature inputs from a desired number "N" of temperature sensing devices in the ablation device, illustrated schematically at 838 and receives electrogram amplitude inputs from a desired number "M" of electrogram monitoring circuits. Each R-F power supply includes a transformer (822, 824, 826), a power control circuit (810, 812, 814) and a power measurement circuit (816, 818, 820). A crystal-locked radio-frequency oscillator 264 generates the switching pulses, which drive both the power transformers (822, 824, 826) and the power controllers (810, 812, 814). Power controllers (810, 812, 814) may be analog controllers which operate by pulse-width modulation by comparing a power set point signal from microprocessor 800 with an actual power signal generated by a power measurement circuit (816, 818, 820), which may, for example, include a torroidal transformer coupled to the power output from the associated transformer (822, 824, 826). The power measurement circuits (816, 818, 820) multiply the output current and voltage and provide the resulting actual power signal to both the power controllers (810, 812, 814) and the microprocessor 800.

The R F power output of the transformers (822, 824, 826) is provided to interface board 808, and thereby is provided to the ablation electrode or electrodes on the ablation device 838. Separate analog comparator circuits (not illustrated) may also be provided for monitoring the output of the power measurement circuits (816, 818, 820), in order to shut-off current to the output transformers (822, 824, 826) if the power exceeds a limit, typically 55 watts. Power transformers (822, 824, 826) may include center taps, which receive the outputs of the power controllers (810, 812, 814). Secondary windings of the transformers (822, 824, 826) may provide for continuous monitoring of the applied voltage in order to permit the power calculations by power measurement circuits (816, 818, 820).

The illustrated power R-F generator system employs software controlled temperature processing, accomplished by micro processor 800, which receives the "N" temperature input signals from temperature measurement circuits (828, 830, 832), each of which are coupled to a corresponding temperature sensor in ablation device 838 by means of an electrical connector, illustrated schematically at 836 and interface circuit 834. If programmed to operate in the temperature controlled mode, processor 800 receives the "N" temperature signals and, based upon the indicated temperatures, defines power set points for each of the power control circuits (810, 812, 814), which in the manner described above control the power levels applied to electrodes on the catheter through interface 834. Processor 800 may also selectively enable or disable any of the "M" provided R-F power sup plies, in response to external control signals from controls 802 or in response to detected anomalous temperature conditions.

In addition to the circuitry as described above and disclosed in the Maguire, et al. '961 patent, the apparatus of FIG. 4 includes multiple electrogram monitoring circuits EGM1, EGM2 . . . EGMM (843, 845 and 847 respectively), which may include one or more peak detectors coupled to sample and hold circuits, operating generally as described in U.S. Pat. No. 6,266,566 issued to Nichols, et al., U.S. Pat. No. 6,029,986 issued to Kim, et al., U.S. Pat. No. 6,095,150 issued to Panescue, et al. or U.S. Pat. No. 5,685,315, issued to McClure, et al., also all incorporated herein by reference in their entireties. The electrogram monitoring circuits measure electrogram amplitudes sensed using electrodes on the RF ablation device. Measured amplitudes may be peak-to-peak measurements of depolarization wave amplitudes or absolute peak value measurements, positive peak vales or negative peak values. Amplitude measurements employed in practicing the invention may be individually measured values or digitally filtered values obtained by averaging a series of individually measured amplitudes. The electrogram signals from the electrodes on the ablation device 838 may first be filtered through low-pass filters F1, F2, . . . FN (842, 844, 846) and may be measured between the ablation electrodes or between electrodes located adjacent the ablation electrodes. Measurements are preferably made during interruptions in the delivery of ablation energy to the ablation electrodes, to minimize noise-sensing problems. Optionally, an EGM trigger circuit 880, coupled to surface EGM electrodes 852 and 854, may trigger electrogram measurement.

Individual electrogram amplitude measurements made by measurement circuits 843, 845 and 847 are provided to the address/data bus 806 and thence to microprocessor 800 for analysis to determine whether the behavior of the measured electrogram amplitude over time, indicates that the lesion associated with the measured amplitudes is completely transmural. As discussed in more detail below, a determination of transmurality may be made in response to detection of a defined drop in electrogram amplitude and/or a series of amplitude measurements that are relatively constant, over a desired period of time or over a defined number of successive amplitude measurements. In some embodiments, an abrupt drop in electrogram amplitude may also be employed to reduce the power level of ablation energy delivered to the tissue being monitored.

In cases in which an alternative ablation energy generation apparatus is employed, particularly those in which a rise in tissue temperature is induced, e.g. laser, microwave or thermal ablation, the R-F generation circuitry of FIG. 4 would be replaced with a corresponding alternative ablation energy generation apparatus. The measurement of electrogram amplitude and its use according to the present invention, however, may still be useful in conjunction with these alternative ablation energy generation systems. Similarly, he measurement of electrogram amplitude and its use according to the present invention may also be useful in conjunction with other forms of ablation such as cryo-ablation, ultrasound ablation and chemical ablation.

Figure 5:
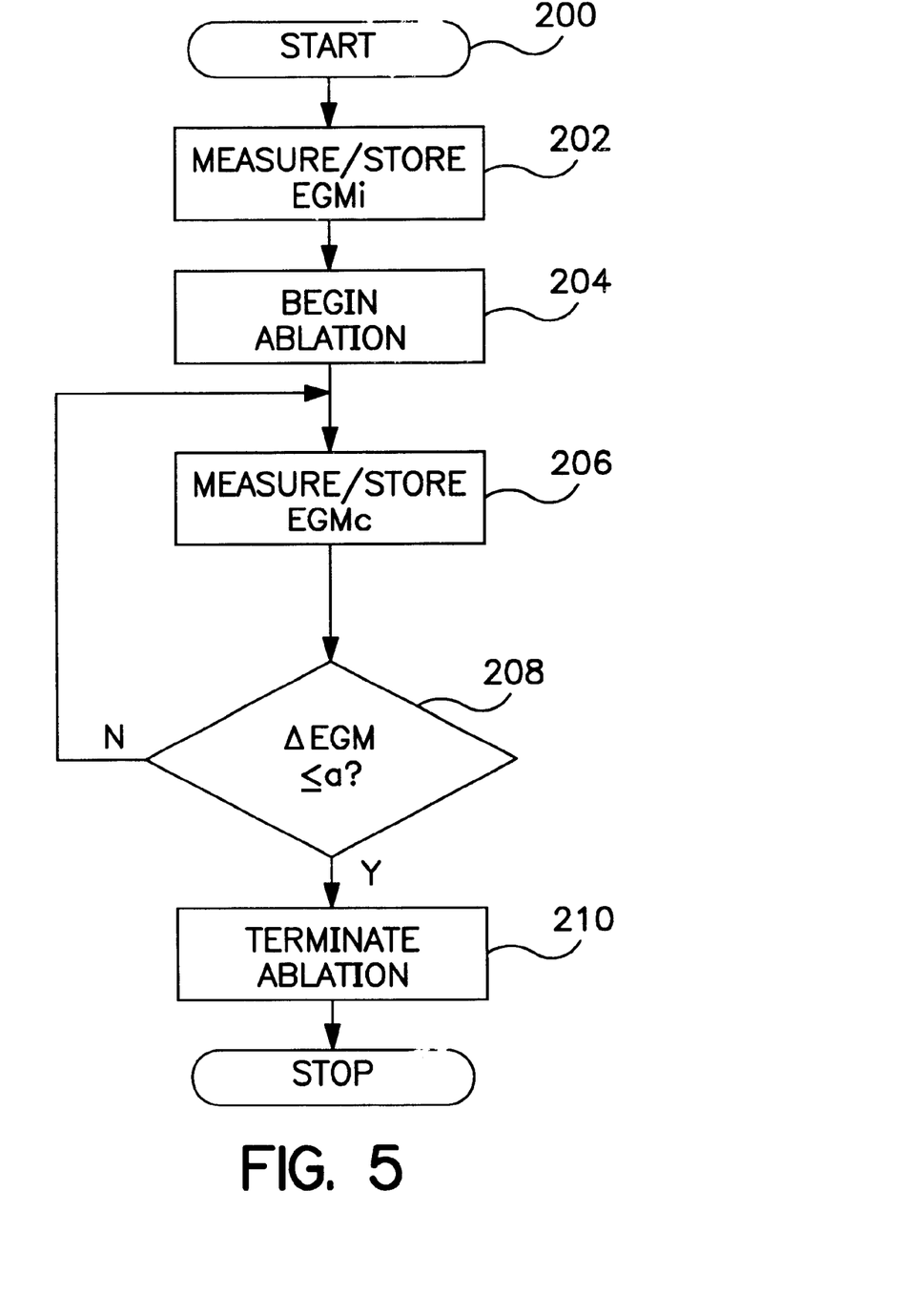
FIG. 5 is a functional flow chart illustrating a first mode of operation of the device illustrated in FIG. 4 in practicing the present invention.

FIG. 5 is a functional flow chart illustrating the operation of a device as in FIG. 4, according to the present invention. The flow chart of FIG. 5 illustrates operation of the device of FIG. 4 to control provision of R-F energy to an individual electrode or electrode pair. In the event that multiple electrodes or electrode pairs are employed, the control methodology of FIG. 5 would be applied to each electrode or electrode pair individually, as discussed in more detail below in conjunction with FIGS. 10 and 11.

The flow chart of FIG. 5 illustrates a method of assessing transmurality and terminating delivery of ablation energy to an electrode or an electrode pair responsive to detection of a specified drop in electrogram amplitude, e.g. a 75% drop. Following the detection of required amplitude drop, the device may wait a defined time period to assure completion of the lesion and then terminate the application of ablation energy to the associated electrode pair. Alternatively, termination of application of ablation energy may occur concurrent with detection of the required amplitude drop. Measurement of electrogram amplitude in tissue adjacent with the ablation electrode or electrode pair electrode pair may be made using the ablation electrodes themselves or using electrodes located in proximity to the ablation electrodes, for example corresponding to those used to measure impedance in the described in Yates '671 patent, incorporated by reference above.

After initialization at 200, the microprocessor 800 (FIG. 4) causes the electrogram measurement circuitry associated with the electrode or electrode pair being evaluated to acquire a base line or initial amplitude value $EGM_i$ at 202. The microprocessor then begins application of ablation energy to the monitored tissue at 204. During application of ablation energy, at defined intervals or in response to trigger signals from an EGM trigger circuit (850, FIG. 4) the microprocessor obtains and stores electrogram measurements at 206. Delivery of ablation energy may be interrupted during the electrogram measurement period. With each obtained amplitude measurement, the processor determines whether the required amplitude drop has occurred. This determination may be made, for example, in response to the first amplitude measurement below a preset required drop value "a", e.g. −75%, to a series of a required number of measured amplitudes below the required drop value, e.g. 2 or 3 measurements, or to a required proportion of measured amplitudes below the required drop value, e.g. 2 of 3 measurements. Alternatively, as noted above, averaged amplitudes may be calculated with each measurement, in which case a drop in the averaged amplitude may be employed to detect transmurality. Ablation and electrogram measurement continues until the required drop has been detected at 208. The termination of application of ablation energy to the tissue being monitored then occurs at 210. The termination of ablation may occur concurrent with detection of the required drop or a preset delay thereafter to assure complete transmurality.

Figure 6:
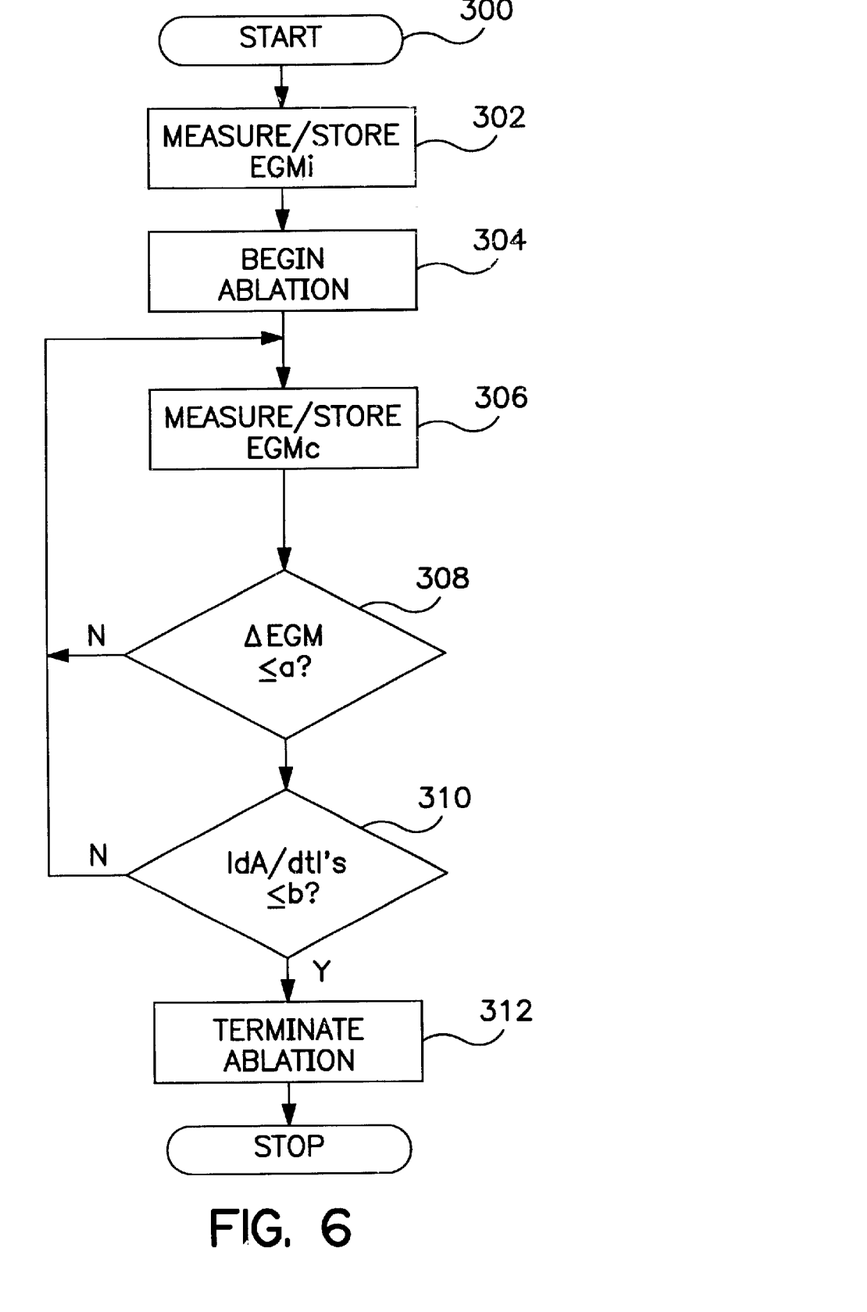
FIG. 6 is a functional flow chart illustrating a first alternative mode of operation of a device as in FIG. 4 in practicing the present invention.

FIG. 6 is a functional flow chart illustrating the operation of a device as in FIG. 4, according to a second embodiment of the present invention. The flow chart of FIG. 6 illustrates operation of the device of FIG. 4 to control provision of R-F energy to an individual electrode or electrode pair. In the event that multiple electrodes or electrode pairs are employed, the control methodology of FIG. 6 would be applied to each electrode or electrode pair individually, as discussed in more detail below in conjunction with FIGS. 10 and 11.

The flow chart of FIG. 6 illustrates a method of assessing transmurality and terminating delivery of ablation energy to an electrode or an electrode pair responsive to detection of a specified drop in electrogram amplitude, e.g. a 75% drop in conjunction with detection of an electrogram amplitude plateau. Following the detection of the required amplitude drop and plateau, the device may wait a defined time period to assure completion of the lesion and then terminate the application of ablation energy to the associated electrode pair. Alternatively, termination of application of ablation energy may occur concurrent with detection of the required amplitude drop and plateau. Measurement of electrogram amplitude in tissue adjacent with the ablation electrode or electrode pair electrode pair may be made using the ablation electrodes themselves or using electrodes located in proximity to the ablation electrodes.

After initialization at 300, the microprocessor 800 (FIG. 4) causes the electrogram measurement circuitry associated with the electrode or electrode pair being evaluated to acquire a baseline or initial amplitude value $EGM_i$ at 302. The microprocessor then begins application of ablation energy to the monitored tissue at 304. During application of ablation energy, the microprocessor obtains and stores electrogram measurements at 306, as discussed above in conjunction with FIG. 5. With each obtained amplitude measurement, the processor determines whether the required amplitude drop has occurred at 308. This determination may be made as described above in conjunction with FIG. 5.

If the required drop is detected at 308, at 310, the microprocessor 800 employs the stored electrogram amplitude measurements to calculate dA/dt, which may, for example, be calculated based on net variation of electrogram amplitude over a series of 2 or 3 measurements. As discussed above in conjunction with detection of the required amplitude drop, averaged amplitude values may also be used to calculate dA/dt. The absolute value of dA/dt, i.e., |dA/dt| may employed to assess whether or not an electrogram amplitude plateau has been reached at 310, for example by verifying that a series of values of |dA/dt| are all (e.g. 3 of 3) or predominantly (e.g. 2 of 3) below a defined variability value "b".

The processor continues to collect amplitude measurements and make calculations until such time as an amplitude plateau is recognized at 310 and a sufficient amplitude drop is recognized at 308. When both of these criteria have been met, the termination of application of ablation energy to the tissue being monitored then occurs at 312. The termination of ablation may occur concurrent with detection of the required drop or a preset delay thereafter to assure complete transmurality.

Figure 7:
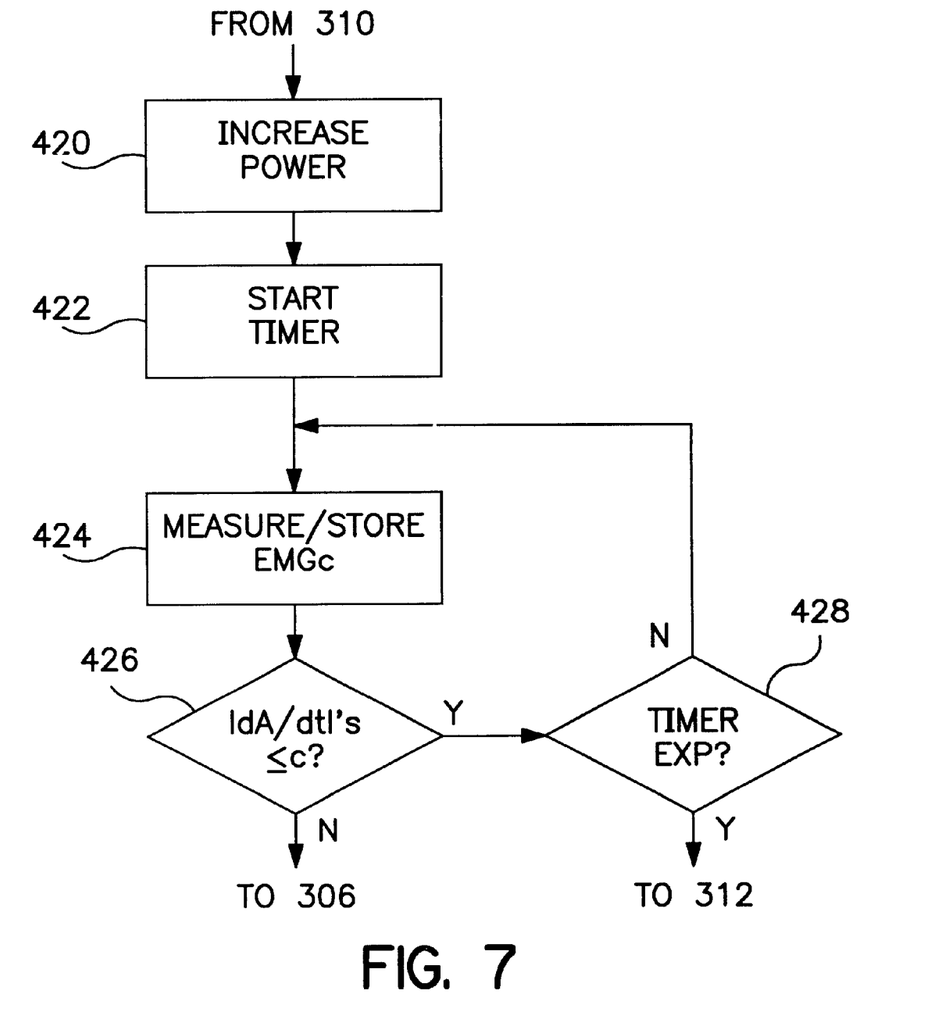
FIG. 7 is a functional flow chart illustrating a modification to the mode of operation according to FIG. 6.

FIG. 7 is a functional flow chart illustrating an optional additional set of operations for implementing a transmurality measurement method generally as in FIG. 6. The additional operations provide for an increase in ablation energy responsive to detection of an electrogram amplitude plateau at 310 (FIG. 6), in order to verify that ablation is complete. The processor triggers an increase in power at 420, for example 5 to 25%, and starts time period of a few seconds at 422. Measurement and calculation of electrogram amplitudes continues at 424 until either a significant drop in amplitude is detected at 426 or the timer expires at 428. If a significant drop is detected, for example the same magnitude of drop that would have prevented plateau detection at 310 (FIG. 6), the processor re-initiates the process of detecting a plateau at 306 (FIG. 6). If the time period expires with no further significant drop in electrogram amplitude, the processor terminates the ablation process at 312 (FIG. 6).

Figure 8:
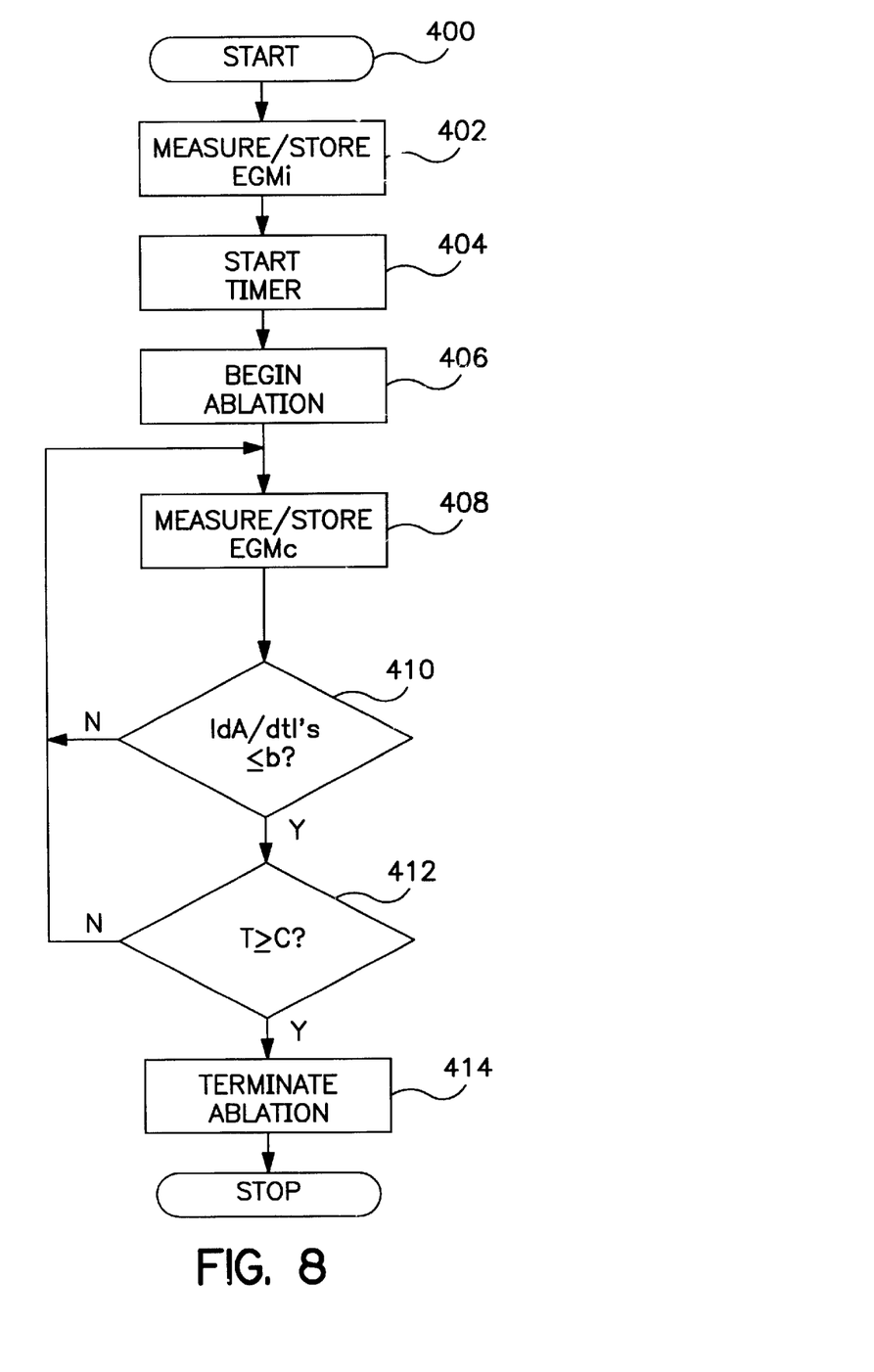
FIG. 8 is a functional flow chart illustrating a second alternative mode of operation of a device as in FIG. 4 in practicing the present invention.

FIG. 8 is a functional flow chart illustrating the operation of a device as in FIG. 4, according to an additional alternative embodiment of the present invention. The flow chart of FIG. 8 illustrates operation of the device of FIG. 4 to control provision of R-F energy to an individual electrode or electrode pair. In the event that multiple electrodes or electrode pairs are employed, the control methodology of FIG. 8 would be applied to each electrode or electrode pair individually, as discussed in more detail below in conjunction with FIGS. 10 and 11.

The flow chart of FIG. 8 illustrates a method of assessing transmurality and terminating delivery of ablation energy to an electrode or an electrode pair responsive to detection of an electrogram amplitude plateau in conjunction with a defined minimum ablation duration. Following the detection of the required plateau, the device may wait a defined time period to assure completion of the lesion and then terminate the application of ablation energy to the associated electrode pair. Alternatively, termination of application of ablation energy may occur concurrent with detection of the required amplitude drop and plateau. Measurement of electrogram amplitude in tissue adjacent with the ablation electrode or electrode pair electrode pair may be made using the ablation electrodes themselves or using electrodes located in proximity to the ablation electrodes.

After initialization at 400, the microprocessor 800 (FIG. 4) causes the electrogram measurement circuitry associated with the electrode or electrode pair being evaluated to acquire a base line or initial amplitude value $EGM_i$ at 402. The microprocessor then starts a duration time interval at 404 and begins application of ablation energy to the monitored tissue at 406. During application of ablation energy, the microprocessor obtains and stores electrogram measurements at 408, as discussed above in conjunction with FIG. 5. With each obtained amplitude measurement, the processor 800 determines whether an amplitude plateau has occurred at 410, in the manner discussed above in conjunction with FIG. 6. If a plateau is detected, the processor check to see if the required minimum ablation time, e.g. 10 seconds, has elapsed at 412.

The processor continues to collect amplitude measurements until such time as an amplitude plateau is recognized at 410 and a sufficient time has elapsed at 412. When both of these criteria have been met, the termination of application of ablation energy to the tissue being monitored then occurs at 414. The termination of ablation may occur concurrent with detection of the required drop or a preset delay thereafter to assure complete transmurality.

Figure 9A:
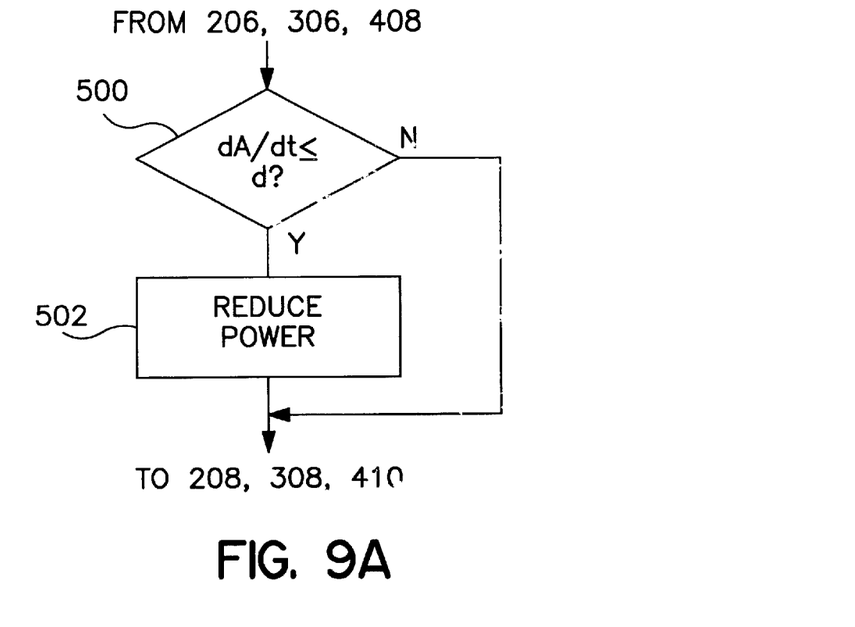
FIG. 9A is a functional flow chart illustrating a modification to the modes of operation according to FIGS. 5, 6 and 8.

FIG. 9A illustrates an additional set of operations for implementing a transmurality measurement method generally as in FIGS. 5, 6 or 8. The operations of FIG. 8 may be performed following the measurement of electrogram amplitude at 206, 306 or 408 (FIGS. 5, 6 and 8). In the additional operations illustrated in FIG. 9A, the microprocessor checks at 500 to determine whether electrogram amplitude is decreasing too rapidly, for example in response to dA/dt having a value less than a defined negative threshold "d", e.g. −10 mv/s. In response to a detected excessive decrease at 500, the processor reduces the power level of the ablation energy being applied to the monitored tissue at 502 to slow the ablation process. Operation of the device then continues as in FIGS. 5, 6 or 8.

Figure 9B:
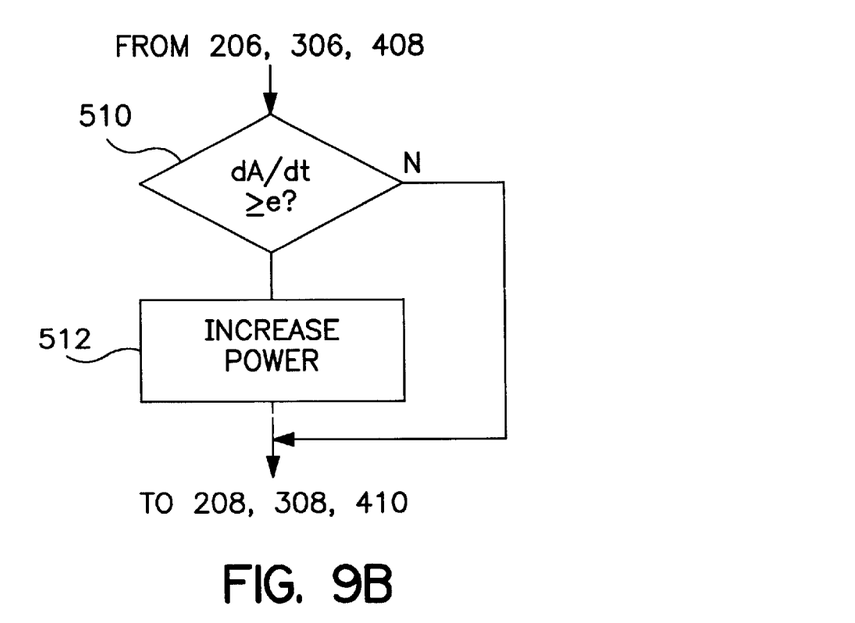
FIG. 9B is a functional flow chart illustrating an additional modification to the modes of operation according to FIGS. 5, 6 and 8.

FIG. 9B also illustrates an additional set of operations for implementing a transmurality measurement method generally as in FIGS. 5, 6 or 8. The operations of FIG. 8 may be performed following the measurement of electrogram amplitude at 206, 306 or 408 (FIGS. 5, 6 and 8) and may be performed in conjunction with or instead of the operations of FIG. 9A. In the additional operations illustrated in FIG. 9B, the microprocessor checks at 510 to determine whether electrogram amplitude is decreasing too rapidly, for example in response to dA/dt having a value greater than a defined negative threshold "e", e.g. −1 mv/s. In response to a detected insufficient decrease at 510, the processor increases the power level of the ablation energy being applied to the monitored tissue at 512 to speed the ablation process. Operation of the device then continues as in FIGS. 5, 6 or 8.

Figure 10:
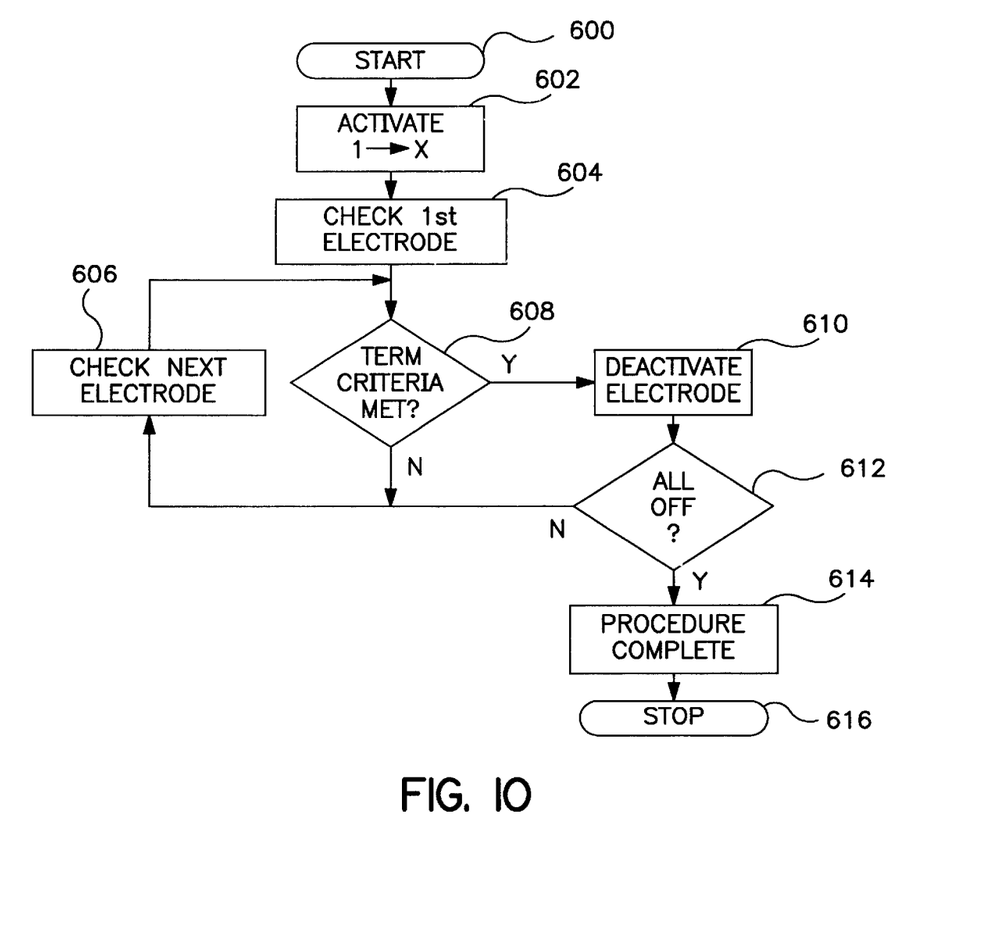
FIG. 10 is a functional flow chart illustrating a first method of operation of a device as in FIG. 4 to activate and deactivate individual electrodes or electrode pairs.

FIG. 10 is a functional flow chart illustrating the over-all operation of the device in conjunction with a multi electrode or multi electrode pair ablation apparatus. In the flow chart of FIG. 10, all the ablation electrodes or electrode pairs are activated simultaneously and individual ablation electrodes or electrode pairs are deactivated in response to electrogram amplitude measurements associated with the electrode pair indicating that the lesion formed between that electrode pair is completely transmural. In this circumstance, the ablation system works as follows.

After initialization at 600, all electrodes 1–X are activated at 602, meaning that ablation energy is provided to all electrodes and electrode pairs. The microprocessor measures the electrogram amplitude associated with a first electrode or electrode pair at 604 and then at 608 checks to see whether transmurality criteria are met for a first ablation electrode or electrode pair at 604, using the criteria discussed above in conjunction with any of FIGS. 5–8. If so, the ablation electrode or electrode pair is deactivated at 610 by ceasing the delivery of ablation energy to the electrode or electrode pair. If not, the microprocessor measures the electrogram amplitude associated with the next ablation electrode or electrode pair at 606 and checks transmurality criteria for the next electrode at 608. This process continues until all electrodes are deactivated at 612, after which the procedure is deemed complete at 614 and the ablation process is terminated at 616.

Figure 11:
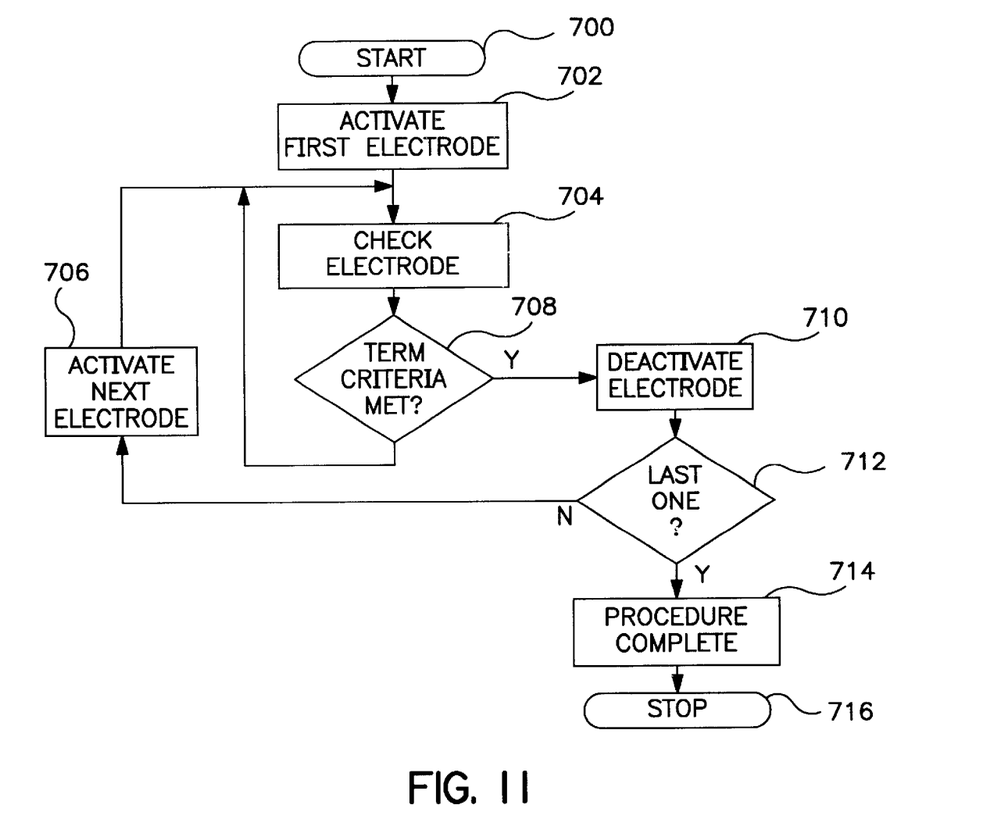
FIG. 11 is a functional flow chart illustrating a second method of operation of a device as in FIG. 4 to activate and deactivate individual electrodes or electrode pairs.

FIG. 11 illustrates a functional flow chart of overall operation of a device in which a multi-electrode or multi-electrode pair ablation apparatus is employed, as in FIG. 10. In this embodiment, however, ablation electrodes or electrode pairs are activated sequentially. After initialization at 700, the microprocessor activates delivery of ablation energy to the first ablation electrode o electrode pair at 502 and measures electrogram amplitude at 604. At 608, the processor and, in the same manner as described for FIG. 9 above, checks to determine whether transmurality criteria have been met. If so, the ablation electrode or electrode pair is deactivated at 610. If not, application of ablation energy continues until the transmurality criteria are met as described above. After deactivation of an electrode or electrode pair at 610, the microprocessor checks to determine whether all electrodes have been activated and deactivated at 612, if not, the microprocessor then activates the next electrode or electrode pair at 606 and initiates delivery of ablation energy to that electrode or electrode pair. This process continues until the last electrode has been deactivated at 612, following which the microprocessor determines that the ablation process is complete at 614 and the ablation process is stopped at 616.

The overall operational methodology of FIG. 10 is believed to be desirable in that it allows for a more rapid completion of an ablation procedure. However, the overall operational method is described in FIG. 11 has the advantage that it may allow the use of a somewhat simplified generator because that multiple, separate electrogram measurement circuits, power control circuits, and the like need not be provided for each electrode or electrode pair. A simple switching mechanism may be used in conjunction with only a single RF generator and electrogram measurement circuit to successively apply energy to each electrode and to monitor electrogram amplitude according to the invention.

In conjunction with the above specification, we claim:

1. An ablation system, comprising:
   generating means for generating ablation energy;
   an ablation device comprising ablation means connectable to the generating means and locatable adjacent a tissue site to be ablated, for applying the generated ablation energy to the tissue site;
   an electrogram measuring electrode mounted to the ablation device so that the electrogram measuring electrode is adjacent the tissue site when the ablating means is adjacent the tissue site;
   electrogram amplitude measurement circuitry connectable to the electrogram measuring electrode to measure electrogram amplitude at the tissue site, using the electrogram measuring electrode; and
   control circuitry operably coupled to the generating means to initiate and terminate the application of ablating energy to the ablating means, wherein the control circuitry is coupled to the electrogram amplitude measurement circuit and terminates application of ablation energy to the ablating means responsive to occurrence of a plateau in the electrogram amplitude measured by the electrogram amplitude measuring circuitry following initiation of application of ablating energy to the ablating means.

2. A system as in claim 1 wherein the first ablating means is an ablation electrode and wherein the generating means comprises an R-F generator.

3. A system as in claim 2 wherein the ablation electrode is an irrigated ablation electrode.

4. A system as in claim 2 wherein the ablation electrode is employed as the electrogram-measuring electrode.

5. An ablation system, comprising:
   generating means for generating ablation energy;
   an ablation device comprising ablation means connectable to the generating means and locatable adjacent a tissue site to be ablated, for applying the generated ablation energy to the tissue site;
   an electrogram measuring electrode mounted to the ablation device so that the electrogram measuring electrode is adjacent the tissue site when the ablating means is adjacent the tissue site;
   electrogram amplitude measurement circuitry connectable to the electrogram measuring electrode to measure electrogram amplitude at the tissue site, using the electrogram measuring electrode; and
   control circuitry operably coupled to the generating means to initiate and terminate the application of ablating energy to the ablating means, wherein the control circuitry is coupled to the electrogram amplitude measurement circuit and reduces the level of ablation energy to the ablating means responsive to occurrence of a rapid drop in the electrogram amplitude measured by the electrogram amplitude measuring circuitry following initiation of application of ablating energy to the ablating means.

6. A system as in claim 5 wherein the ablating means is an ablation electrode and wherein the generating means comprises an R-F generator.

7. A system as in claim 6 wherein the ablation electrode is an irrigated ablation electrode.

8. A system as in claim 5 wherein the ablation electrode is employed as the electrogram-measuring electrode.

9. An ablation system, comprising:
   generating means for generating ablation energy;
   an ablation device comprising ablation means connectable to the generating means and locatable adjacent a tissue site to be ablated, for applying the generated ablation energy to the tissue site;
   an electrogram measuring electrode mounted to the ablation device so that the electrogram measuring electrode is adjacent the tissue site when the ablating means is adjacent the tissue site;
   electrogram amplitude measurement circuitry connectable to the electrogram measuring electrode to measure electrogram amplitude at the tissue site, using the electrogram measuring electrode; and control circuitry operably coupled to the generating means to initiate and terminate the application of ablating energy to the ablating means, wherein the control circuitry is coupled to the electrogram amplitude measurement circuit and terminates the application of ablation energy to the ablating means responsive to occurrence of a drop in the electrogram amplitude measured by the electrogram amplitude measuring circuitry following initiation of application of ablating energy to the ablating means.

10. A system as in claim 9 wherein the ablating means is an ablation electrode and wherein the generating means comprises an R-F generator.

11. A system as in claim 10 wherein the ablation electrode is an irrigated ablation electrode.

12. A system as in claim 9 wherein the ablation electrode is employed as the electrogram-measuring electrode.

13. A method of ablation, comprising:

applying ablation energy to a tissue site;

monitoring electrogram amplitude at the tissue site while applying ablation energy; and responsive to occurrence of an electrogram amplitude plateau, terminating application of ablating energy to the tissue site.

14. A method as in claim 13 wherein the applying of ablation energy to the tissue site comprises applying R-F energy using an R-F electrode.

15. A method as in claim 14 wherein the monitoring of electrogram amplitude at the tissue site comprises monitoring electrogram amplitude using the R-F electrode.

16. A method as in claim 15 wherein the applying of R-F energy to the tissue site comprises applying R-F energy using an irrigated R-F electrode.

17. A method of ablation, comprising:

applying ablation energy to a tissue site;

monitoring electrogram amplitude at the tissue site while applying ablation energy; and responsive to occurrence of a rapid drop in electrogram amplitude, reducing the level of ablating energy applied to the tissue site.

18. A method as in claim 17 wherein the applying of ablation energy to the tissue site comprises applying R-F energy using an R-F electrode.

19. A method as in claim 18 wherein the monitoring of electrogram amplitude at the tissue site comprises monitoring electrogram amplitude using the R-F electrode.

20. A method as in claim 19 wherein the applying of R-F energy to the tissue site comprises applying R-F energy using an irrigated R-F electrode.

* * * * *